United States Patent
Radwanski et al.

(10) Patent No.: US 11,383,015 B2
(45) Date of Patent: Jul. 12, 2022

(54) SYSTEM AND METHOD FOR PLASMA PURIFICATION PRIOR TO MONONUCLEAR CELL COLLECTION

(71) Applicant: Fenwal, Inc., Lake Zurich, IL (US)

(72) Inventors: Katherine N. Radwanski, Highland Park, IL (US); Lan T. Nguyen, Vernon Hills, IL (US); Jonathan W. Prendergast, Palatine, IL (US)

(73) Assignee: Fenwal, Inc., Lake Zurich, IL (US)

( * ) Notice: Subject to any disclaimer, the term of this patent is extended or adjusted under 35 U.S.C. 154(b) by 272 days.

(21) Appl. No.: 15/390,549

(22) Filed: Dec. 26, 2016

(65) Prior Publication Data
US 2017/0197023 A1   Jul. 13, 2017

Related U.S. Application Data (60) Provisional application No. 62/277,198, filed on Jan. 11, 2016.

(51) Int. Cl.
| | |
|---|---|
| *A61M 1/36* | (2006.01) |
| *A61M 1/02* | (2006.01) |
| *A61M 1/34* | (2006.01) |
| *A61M 1/26* | (2006.01) |
| *B04B 3/00* | (2006.01) |

(52) U.S. Cl.
CPC ........ *A61M 1/3681* (2013.01); *A61M 1/0209* (2013.01); *A61M 1/262* (2014.02); *A61M 1/3472* (2013.01); *A61M 1/3496* (2013.01); *A61M 1/3679* (2013.01); *A61M 1/3693* (2013.01); *A61M 2202/0443* (2013.01); *A61M 2205/051* (2013.01); *A61M 2205/331* (2013.01); *B04B 3/00* (2013.01)

(58) Field of Classification Search
None
See application file for complete search history.

(56) References Cited

U.S. PATENT DOCUMENTS

| | | | |
|---|---|---|---|
| 5,360,542 A | 11/1994 | Williamson et al. | |
| 6,027,657 A * | 2/2000 | Min | A61M 1/3693 210/782 |
| 6,569,112 B2 | 5/2003 | Strahilevitz | |
| 6,653,293 B1 * | 11/2003 | Miwa | A61P 31/18 514/46 |
| 2002/0128585 A1 * | 9/2002 | Cork | A61B 5/14546 604/6.02 |
| 2013/0197419 A1 * | 8/2013 | Min | A61M 1/30 604/6.01 |
| 2013/0252227 A1 | 9/2013 | Min et al. | |
| 2014/0291248 A1 * | 10/2014 | Foley | A61M 1/3679 210/662 |
| 2014/0370491 A1 * | 12/2014 | Radwanski | A61M 1/3686 435/2 |

FOREIGN PATENT DOCUMENTS

| | | |
|---|---|---|
| EP | 2720730 A2 | 4/2014 |
| WO | 2012/125457 A1 | 9/2012 |
| WO | 2012/141697 A1 | 10/2012 |

OTHER PUBLICATIONS

Hardwick, J. Blood Processing. ISBT Science Series (2008) 3, 148-176. Journal compilation © Blackwell Publishing Ltd. (Year: 2008).*
Dictionary.com. Definition of Hematocrit. (Year: 2019).*
Partial European Search Report for application No. 17150048.1, dated Jun. 2, 2017, 13 pages.
European Patent Office, Extended European Search Report for App. No. 17150048.1, dated Sep. 20, 2017.
Communication pursuant to Article 94(3) EPC for application No. 17150048.1, dated Jul. 19, 2018, 7 pages.

\* cited by examiner

*Primary Examiner* — Nghi V Nguyen
(74) *Attorney, Agent, or Firm* — Cook Alex Ltd.

(57) ABSTRACT

A method of collecting mononuclear cells includes separating plasma from cellular components of whole blood. The cellular components, which include mononuclear cells and red blood cells, are combined with plasma replacement fluid to form a first mixture. The mononuclear cells of the first mixture are separated from the red blood cells of the first mixture, which may be followed by extracorporeal photopheresis being performed on the mononuclear cells.

25 Claims, 6 Drawing Sheets

SYSTEM AND METHOD FOR PLASMA PURIFICATION PRIOR TO MONONUCLEAR CELL COLLECTION

CROSS-REFERENCE TO RELATED APPLICATIONS

This application claims the benefit of U.S. Provisional Patent App. No. 62/277,198 filed Jan. 11, 2016, which is expressly incorporated herein by reference in its entirety.

FIELD OF THE DISCLOSURE

The present disclosure is directed to fluid treatment systems and methods. More particularly, the present disclosure relates to systems and methods for separating blood into its constituents and subsequently treating and/or collecting the constituents.

BACKGROUND

A variety of available blood processing systems allows for the collection and processing of particular blood components, rather than whole blood, from donors or patients. In the case of a blood donor, whole blood is drawn from the donor, a desired blood constituent separated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, mononuclear cells (MNCs), plasma, and/or platelets, etc. In the case of a patient, whole blood is similarly drawn from the patient, a particular blood constituent first separated and then collected and/or treated, and the remaining blood components returned to the patient. The collected and/or treated blood constituent may be saved for future use, returned to the patient, and/or discarded and replaced with a suitable replacement.

The separation of blood components from whole blood typically takes place prior to the collection or treatment of the separated blood component and may be achieved through a spinning membrane or centrifugation, in which whole blood is passed through a centrifuge or membrane after it is withdrawn from the patient. To avoid contamination and possible infection of the patient, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be spun within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of membranes with different pore sizes may be used, depending on the components to be separated.

In the case of MNC collection, which includes the collection of lymphocytes, monocytes, and/or stem cells, MNCs can be removed from the whole blood of a patient, collected, and/or subjected to various therapies. Collected and treated MNCs may then be returned to the patient for the treatment of various blood diseases by, e.g., eliminating immunogenicity in cells, inactivating or killing selected cells, inactivating viruses or bacteria, reconstituting the immune system, and/or activating desirable immune responses. MNC treatments are used for blood or solid organ/tissue cancers, photopheresis treatments, autologous and allogeneic stem cell transplants, donor lymphocyte infusions, research collections, etc.

SUMMARY

According to an exemplary embodiment, the present disclosure is directed to a method of collecting mononuclear cells, comprising separating whole blood into plasma and cellular components, combining the cellular components with plasma replacement fluid to form a first mixture, and separating the first mixture into mononuclear cells and at least one component.

According to an exemplary embodiment, the present disclosure is directed to a method of collecting mononuclear cells, comprising separating whole blood into plasma and cellular components, purifying the plasma through a plasma adsorption column to create purified plasma, combining the cellular components with the purified plasma to form a first mixture, and separating the first mixture into mononuclear cells and at least one component.

According to an exemplary embodiment, the present disclosure is directed to a method of collecting mononuclear cells, comprising providing an adsorption column through which whole blood is flowed to create purified whole blood, and separating the purified whole blood into mononuclear cells and at least one component.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may provide for collecting MNCs with reduced plasma lipid interference during MNC harvest.

Some embodiments may provide for more accurate collection and harvest of MNCs by allowing for a clearer interface between blood component layers.

During harvest of MNCs, non-target substances may be present in the MNC product that can interfere with accurate harvesting of the target MNCs. Plasma proteins and lipids may interfere, for example, in the event that the donor/patient has certain disease states or medications, such as elevated bilirubin levels and drugs such as mycophenolate mofetil (MMF) and cyclosporine, which cause hyperlipidemia.

Figure 1:
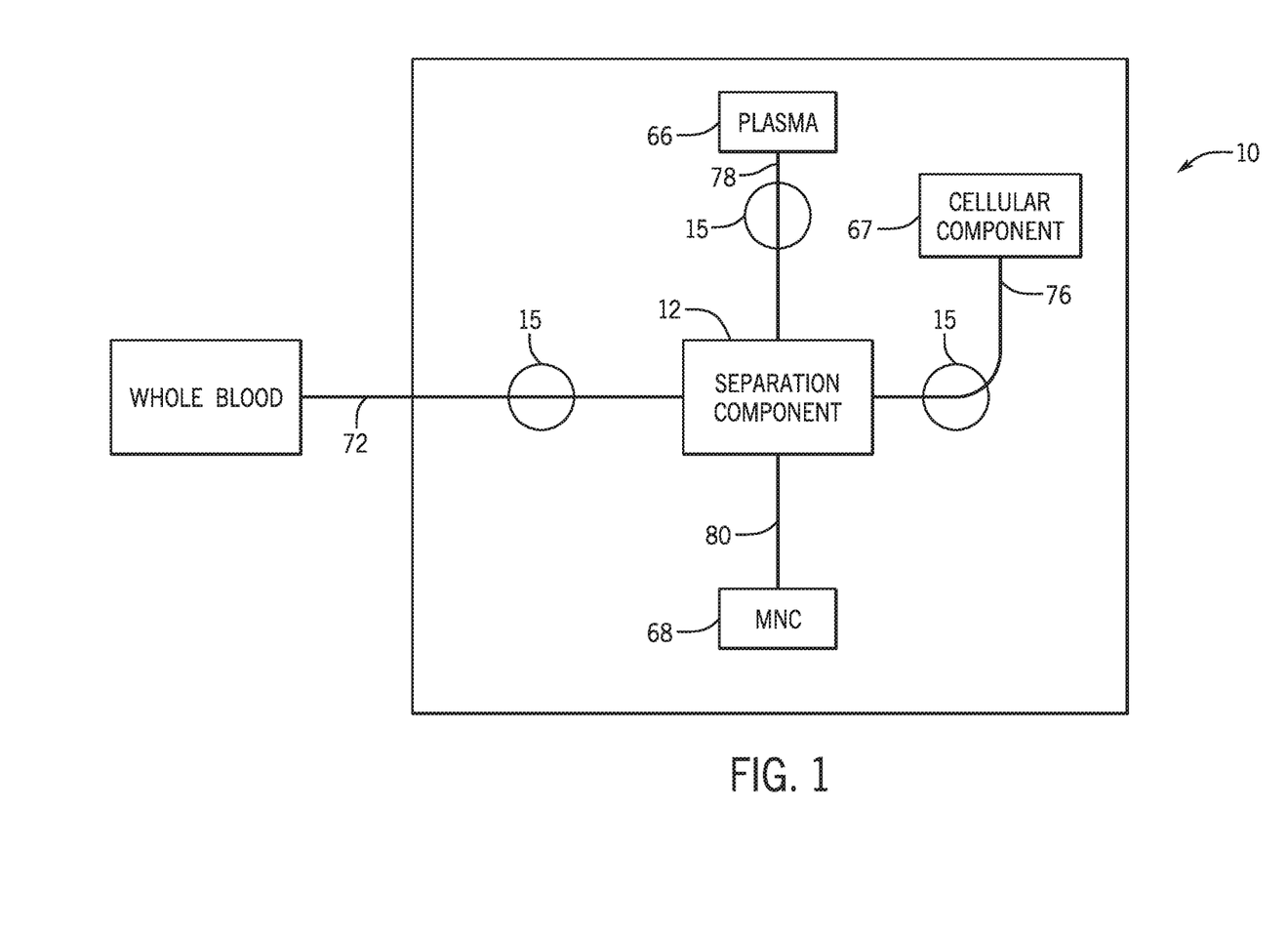
FIG. 1 is a diagrammatic depiction of a separation system useful in the separation and collection of mononuclear cells, according to an exemplary embodiment.
Figure 2:
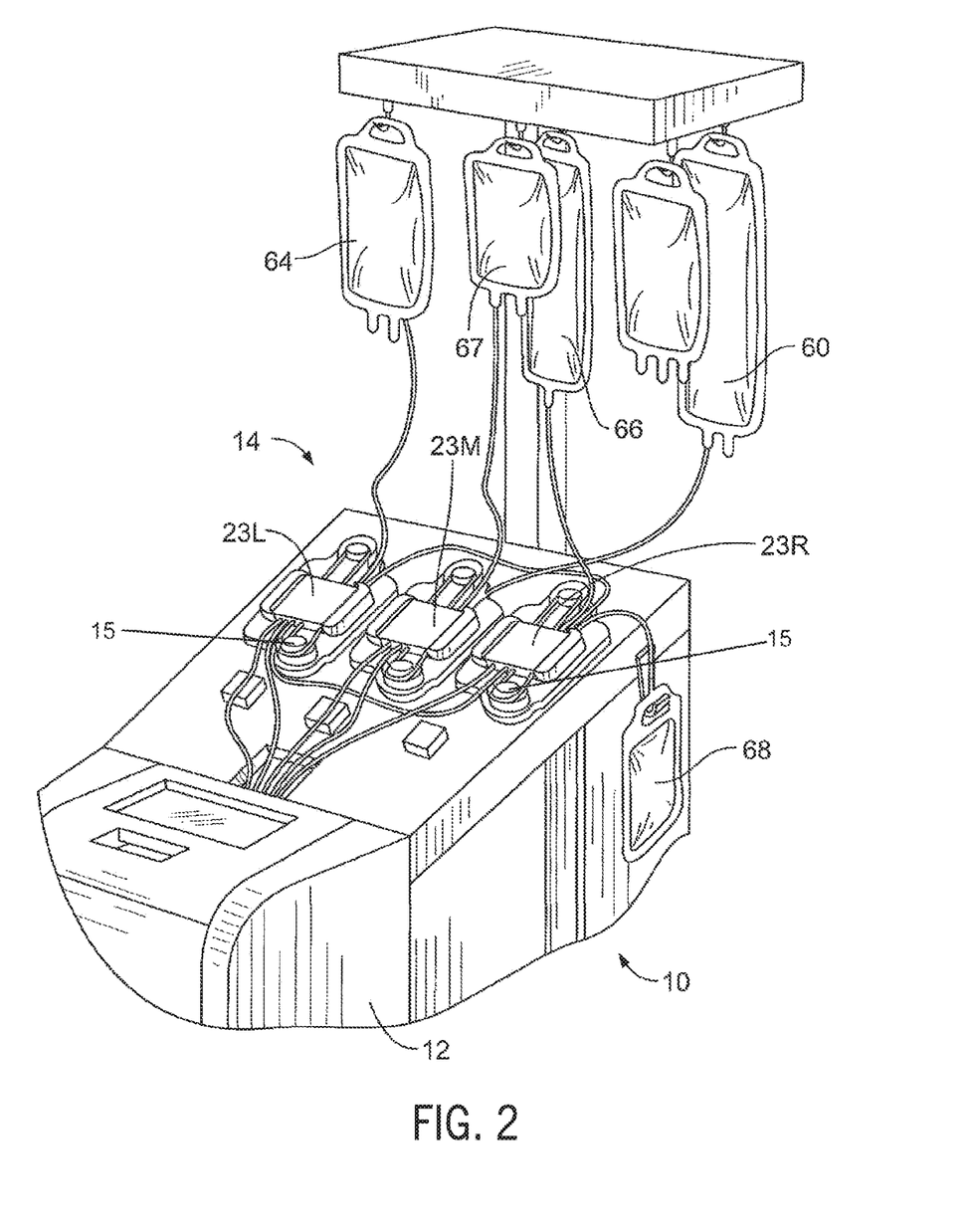
FIG. 2 is a perspective view of the front panel of a separation system with a disposable processing set for collecting mononuclear cells mounted on the device, according to an exemplary embodiment.

FIG. 1 is a diagrammatic depiction of a separation system 10 useful in the separation and collection of mononuclear cells, as described herein, and FIG. 2 shows an exemplary embodiment of the separation system 10, The system 10 may include a separation component 12 and a disposable processing kit 14 (FIG. 2) that is mounted thereon. Flow direction and rate may be controlled by a plurality of pumps 15 engaged with the processing kit 14, In one embodiment, the separation principle used by the separator 12 is based on centrifugation, but an automated separator based on a different separation principle (e.g., spinning membrane, etc.) may also be used.

A patient may be connected to the fluid circuit 14, which may provide a sterile closed pathway between the separation component 12 and the remainder of the processing kit 14, Whole blood that is withdrawn from the patient may be introduced into the separation component 12, where the whole blood may be separated to provide a target cell population, which in the context of the present disclosure may be mononuclear cells. Other components separated from the whole blood, such as red blood cells and platelets may be returned to the patient or collected in pre-attached containers of the blood processing set. The separated target cell population, e.g., mononuclear cells, may then be collected for future use or prepared for various therapies. One example of a therapy involving MNCs that may benefit from reducing plasma lipid interference during MNC harvest is extracorporeal photopheresis or "ECP". ECP involves the extracorporeal exposure of MNCs combined with a photoactive compound, such as 8-methoxypsoralen or "8-MOP" which is then photoactivated by ultraviolet light, followed by re-infusion of the treated MNCs. Removal of plasma lipids, which absorb UV light during irradiation, may lead to generally more consistent and less variable irradiation procedures, thereby enhancing accuracy of irradiation dosing and shortening procedure time.

Apparatus useful in the collection of mononuclear cells, and providing the separation component 12 of FIG. 1, include for example the Amicus® Separator made and sold by Fenwal, Inc., of Lake Zurich, Ill. Mononuclear cell collections using a device such as the Amicus® are described in greater detail in U.S. Pat. No. 6,027,657, the contents of which are incorporated by reference herein in its entirety. The fluid circuit 14 (FIG. 3) may include a blood processing container 16 defining a separation chamber suitable for harvesting MNCs from whole blood.

As shown in FIG. 2, a disposable processing set or fluid circuit 14 (which includes container 16) may be mounted on the front panel of the separation component 12. The processing set (fluid circuit 14) may include a plurality of processing fluid flow cassettes 23L, 23M and 23R with tubing loops for association with peristaltic pumps 15 on the separation component 12. Fluid circuit 14 may also include a network of tubing and pre-connected containers for establishing flow communication with the patient and for processing and collecting fluids and blood and blood components, as shown in greater detail in FIG. 3.

Figure 3:
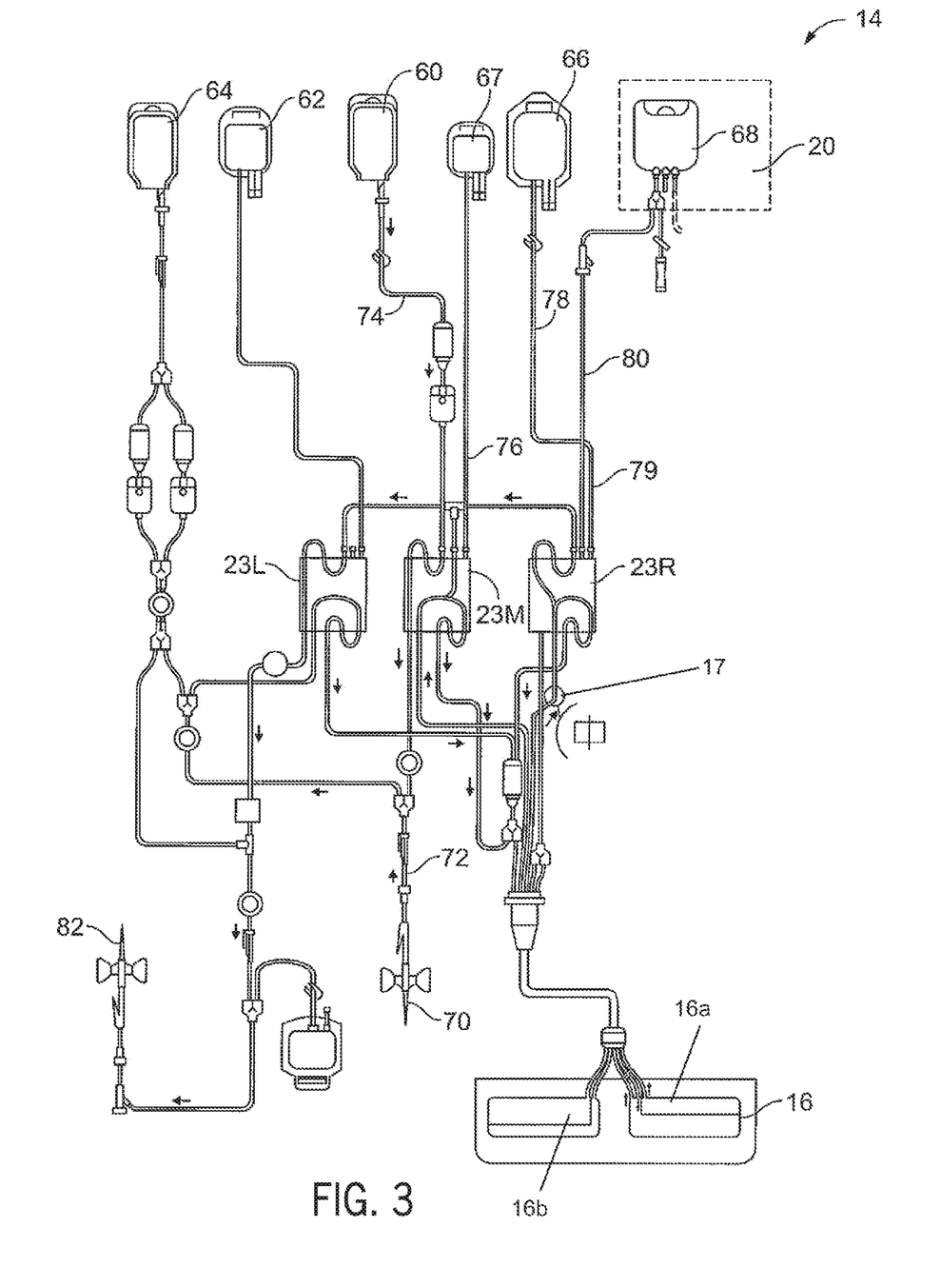
FIG. 3 is a diagram showing the disposable processing set of FIG. 2, according to an exemplary embodiment.

As seen in FIG. 3, the disposable processing set 14 may include a container 60 for supplying anticoagulant, an in-process container 62, a container 64 for holding a crystalloid solution, such as saline, a container 66 for collecting plasma, and a container 68 for collecting the mononuclear cells.

With reference to FIG. 3, fluid circuit 14 may include inlet line 72, an anticoagulant (AC) line 74 for delivering AC from container 60, an RBC line 76 for conveying red blood cells from chamber 16 of set 14 to container 67, a platelet-poor plasma (PPP) line 78 for conveying PPP to container 66 and line 80 for conveying mononuclear cells to and from separation chamber 16 and collection container 68.

The blood processing set may also include one or more venipuncture needle(s) for accessing the circulatory system of the patient. As shown in FIG. 3, fluid circuit 14 may include inlet needle 70 and return needle 82. In an alternative embodiment, a single needle may serve as both the inlet and outlet needle.

Fluid flow through fluid circuit 14 may be driven, controlled and adjusted by a microprocessor-based controller in cooperation with the valves, pumps, weight scales and sensors of separation component 12 and fluid circuit 14, the details of which are described in the previously mentioned U.S. Pat. No. 6,027,657.

A separation chamber may be defined by the walls of the processing container 16. The processing container 16 may comprise two different compartments 16a and 16b (FIG. 3). Using both compartments 16a and 16b for separation in a procedure may enable multiple target products to be separated simultaneously and/or multiple steps to be completed simultaneously. If only one compartment is used for separation, the other compartment may optionally be used as an in-process, waste, or storage container. In operation, the separation device 12 may rotate the processing container 16 about an axis, creating a centrifugal field within the processing container 16. Details of the mechanism for rotating the processing container 16 are disclosed in U.S. Pat. No. 5,360,542 titled "Centrifuge with Separable Bowl and Spool Elements Providing Access to the Separation Chamber," which is also incorporated herein by reference in its entirety.

In one embodiment, an apheresis device or system 10 may include a programmable controller that is pre-programmed with one or more selectable protocols. A user/operator may select a particular processing protocol to achieve a desired outcome or objective. The pre-programmed selectable protocol(s) may be based on one or more fixed and/or adjustable parameters. During a particular processing procedure, the pre-programmed controller may operate the separator 12 and processing chamber 16 associated therewith to separate blood into its various components, as well as operate one or more pumps to move blood, blood components and/or solutions through the various openable valves and tubing segments of a processing set, such as processing set 14 illustrated in FIG. 3. The various processing steps performed by the pre-programmed automated apheresis device may occur separately, in series, simultaneously or any combination of these.

An automated apheresis device may be used to perform MNC collection in a batch process in which MNCs continuously collect in the chamber 16 until the target cycle volume is reached. During the continuous collection of MNCs within the chamber 16, different blood components separate into layers that may be detected by an optical interface detector that monitors the location and presence of the interface between layers. Details of an exemplary mechanism for interface detection are disclosed in U.S. Pat. No. 6,027,657, the contents of which are incorporated by reference herein in its entirety. Before and during the transfer of the MNCs out of the chamber 16, MNCs and other blood components (e.g., plasma, etc.) may pass through an optical sensor 17, located downstream of the chamber 16, which detects the presence of cells in the tubing line to determine the start and end of the MNC harvest (i.e. when to open and close the valves leading to the product container). The term "downstream" describes an event proximal to post-separation, and the term "upstream" describes an event proximal to pre-separation. "Downstream" and "upstream" are relative terms, with the reference point being the time/location of separation. After MNC harvest is complete, the remaining cells in the line may be flushed into the product container with a predetermined volume of plasma known as the "plasma flush".

The ability of the interface detector to accurately detect the interface between blood component layers may be facilitated by removal of non-target substances (e.g., plasma proteins and lipids) that may be present in the blood that can interfere with the separation procedure. Additionally, the removal of non-target substances may improve the ability of the optical sensor 17 to accurately detect the presence of cells in the tubing line to determine the start and end of the MNC harvest to facilitate precise harvesting of the target MNCs.

EXAMPLES

Without limiting any of the foregoing, the subject matter described herein may be found in one or more methods, systems and/or products. For example, in a first aspect of the present subject matter, an improved system and method for obtaining MNCs is set forth in FIG. 4. The inlet needle 70 of FIG. 3 attached to inlet line 72 may first be connected to a blood source 5 (e.g., donor, patient, blood bag, etc.). Whole blood may enter the separation chamber 16 of the separator 12, which separates the whole blood into plasma and cellular components. The plasma may be separated and directed into a plasma container 66, and the cellular components may be separated and directed into a different container 67. The separated cellular contents may be combined with a replacement fluid 69 that has minimal non-target content (e.g., plasma proteins and/or lipids) that may interfere with optical sensor readings. Examples of suitable replacement fluids include fresh frozen plasma, immunoglobulin solution, albumin, and/or other colloid solutions. The cellular components mixed with replacement fluid may then be returned to the separation chamber 16, where target MNCs may be collected. The target MNCs may be harvested into a designated container 68 to be processed for further treatment. Non-target components may be collected or returned to the patient/donor.

Figure 4:
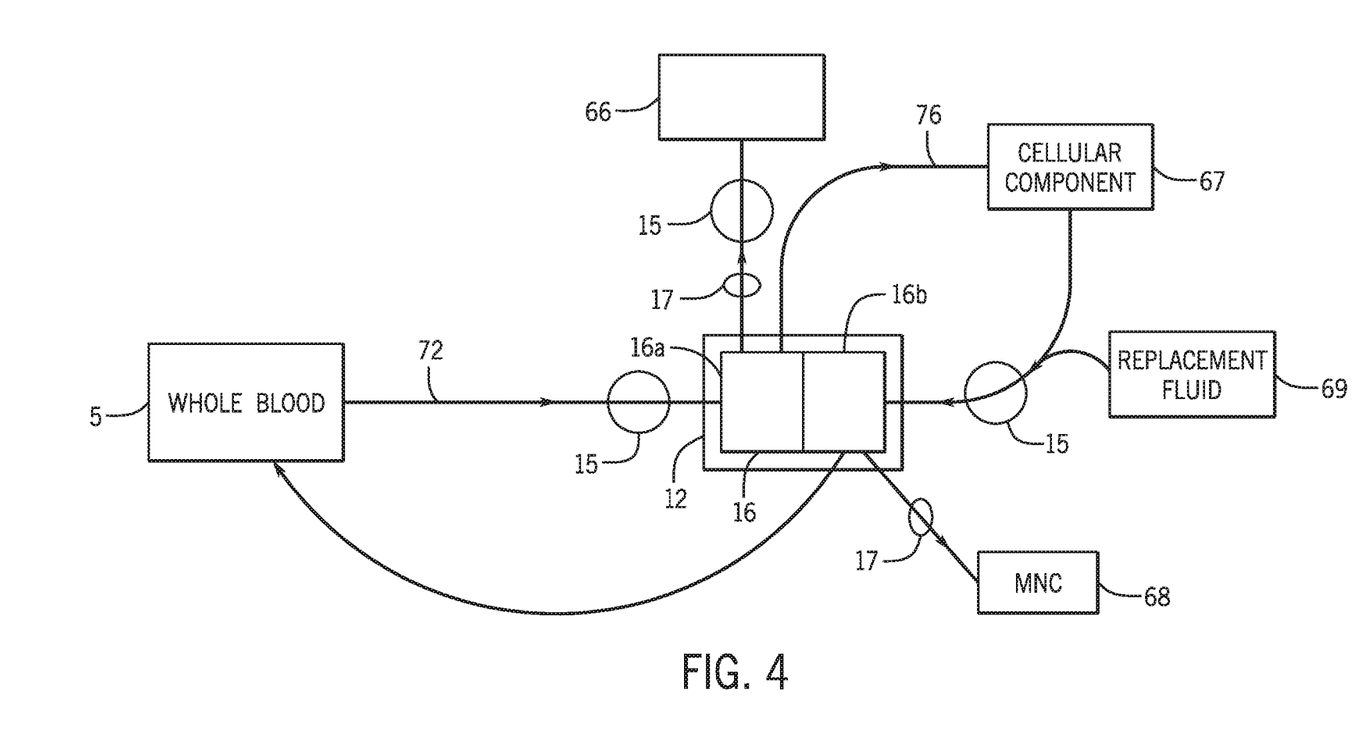
FIG. 4 is a flow diagram illustrating an improved method for obtaining mononuclear cells, according to an exemplary embodiment.

The process and steps of whole blood initially entering the separation chamber 16 and the cellular components and replacement fluid mix returning to the separation chamber 16 portrayed in FIG. 4 may take place substantially in series if only one compartment 16a or 16b is utilized. Alternatively, the process and steps of whole blood entering the separation chamber 16 and the fluid mix returning to the separation chamber 16 may take place substantially at the same time if both compartments 16a and 16b are utilized. In an embodiment in which the processes take place substantially in series, whole blood entering one of the compartments 16a or 16b may separate into plasma and cellular components, both of which may be directed to separate containers until separation of plasma and cellular components is complete. An optical sensor 17 may optionally be placed downstream of the separation chamber 16a and/or 16b at a tubing line leading to the MNC product container 68 and/or leading to the plasma container 66 to determine when plasma is clear enough and plasma diversion can stop. Subsequently, the cellular components may combine with the replacement fluid within one of the compartments 16a or 16b, and further separation into target MNCs and non-target components may take place.

In an embodiment in which the steps of whole blood entering the separation chamber 16 and the fluid mix returning to the separation chamber 16 take place substantially at the same time, whole blood entering a first compartment (e.g., 16a) may separate into plasma and cellular components, with the plasma being sent to an plasma container 62. Simultaneously, the cellular components may join the replacement fluid and together enter a second compartment (e.g., 16b) and there further separate into target MNCs and non-target components. An optical sensor 17 may optionally be placed downstream of the separation chamber 16a at a tubing line leading to the MNC product container 68 and/or leading to the plasma container 66 to determine when plasma is clear enough and plasma diversion can stop. As the replacement fluid continues to enter compartment 16b and the clarity of the plasma leaving compartment 16a improves sufficiently as determined by the optical sensor 17, the plasma diversion from compartment 16a into the plasma container 66 can be stopped, and any unseparated whole blood, including the contents of compartment 16a, may be directed to compartment 16b to continue MNC collection.

Figure 5:
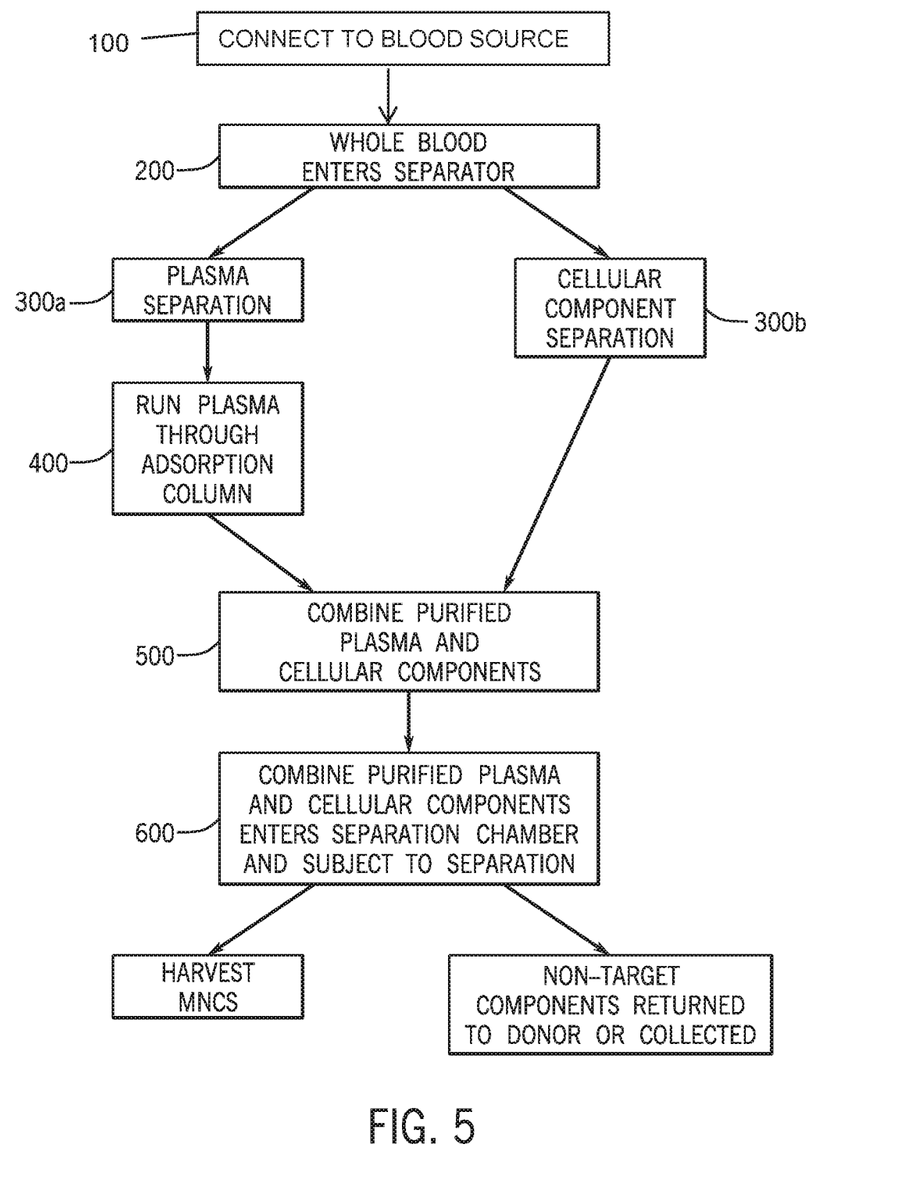
FIG. 5 is a flow diagram illustrating an improved method for obtaining mononuclear cells, according to another exemplary embodiment.

In another aspect of the present subject matter, an improved method for obtaining MNCs is set forth in FIG. 5. An inlet needle may first be connected to a blood source 5 (e.g., donor, patient, blood bag, etc.) at step 100 of FIG. 5. In step 200, whole blood enters a separator, which separates the whole blood into plasma (step 300*a*) and cellular components (step 300*b*). In the embodiment in FIG. 5, the separator of step 200 may be a centrifugal or spinning membrane separator. An exemplary spinning membrane and hardware is disclosed in greater detail in PCT Patent Application No. PCT/US2012/28492, which is incorporated herein by reference in its entirety, although any suitable membrane assembly may be used, Plasma separated in step 300*a* may be flowed through an adsorption column in step 400. An exemplary adsorption column is the MONET filter made and sold by Fresenius Medical Care. Another exemplary adsorption column is disclosed in greater detail in International Publication No, WO 2012/141697 and U.S. Pat. No. 6,569,112, each of which is hereby incorporated by reference herein in its entirety, although any suitable column may be used. In step 500, purified plasma from the adsorption column in step 400 may be combined with the cellular components of step 300*b*. The combined product of step 500 may then be separated in a separation chamber of a separator in step 600 to collect and harvest MNC target cells separated from non-target components.

Figure 6:
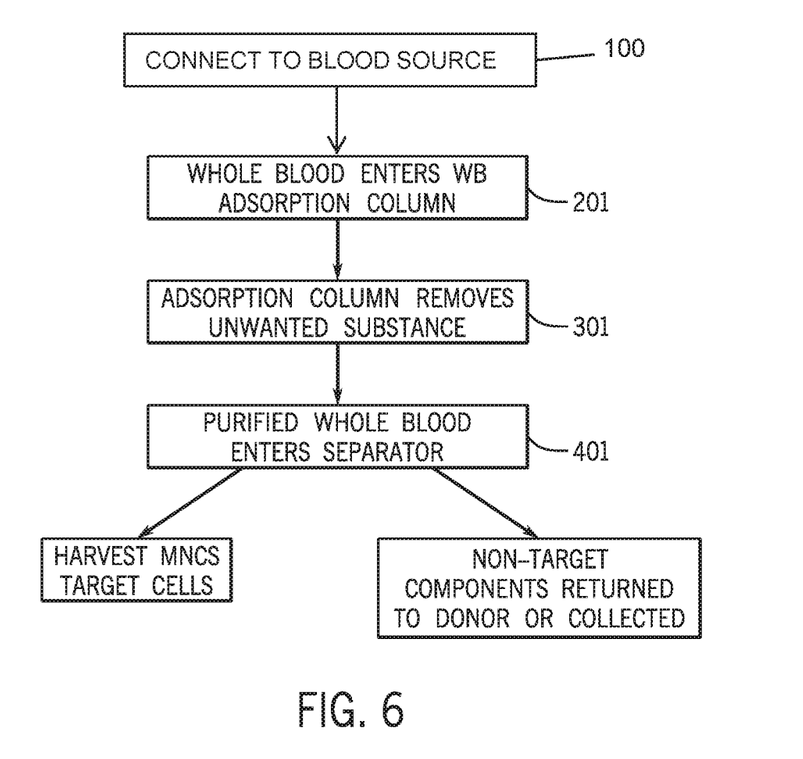
FIG. 6 is a flow diagram illustrating an improved method for obtaining mononuclear cells, according to another exemplary embodiment.

In another aspect of the present subject matter, an improved method for obtaining MNCs is set forth in FIG. 6. An inlet needle may first be connected to a blood source 5 (e.g., donor, patient, blood bag, etc.) at step 101 of FIG. 6. In step 201, whole blood enters a whole blood adsorption column, which removes certain lipids, proteins, antibodies, and/or fatty acids in step 301. An exemplary whole blood adsorption column is the DALI® adsorber made and sold by Fresenius Medical Care, although any suitable whole blood adsorption column may be used. Purified whole blood exiting from the WB adsorption column of step 201 may then be separated in a separation chamber 16 of a separator in step 401 to collect and harvest MNC target cells separated from non-target components.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A method of collecting mononuclear cells, comprising:
separating whole blood into first and second constituents, the first constituent comprising plasma and the second constituent including mononuclear cells and red blood cells;
combining the second constituent with plasma replacement fluid to form a first mixture including the mononuclear cells and the red blood cells; and
separating the mononuclear cells from the red blood cells of the first mixture, wherein
said separating whole blood into first and second constituents includes not separating the mononuclear cells as part of a third constituent, and
said separating the mononuclear cells from the red blood cells of the first mixture includes optically monitoring the first mixture and/or a separated component of the first mixture.

2. The method of claim 1, further comprising the step of performing extracorporeal photopheresis on the mononuclear cells, and wherein the plasma replacement fluid contains fewer proteins, lipids, and/or bilirubin than does the plasma.

3. The method of claim 1, wherein the step of separating whole blood into first and second constituents is performed by a centrifugal separator.

4. The method of claim 3, furthering comprising the steps of separating the whole blood within a compartment of a separation chamber, directing the first and second constituents to separate containers until separation of the whole blood is complete, directing the first mixture into the compartment, and separating the mononuclear cells from the red blood cells of the first mixture in the compartment.

5. The method of claim 4, wherein the steps of separating whole blood into first and second constituents and separating the mononuclear cells from the red blood cells of the first mixture take place substantially in series.

6. The method of claim 3, further comprising the steps of separating the whole blood within a first compartment of a separation chamber, directing the first constituent to a container, directing the first mixture to a second compartment of the separation chamber, and separating the mononuclear cells from the red blood cells of the first mixture within the second compartment.

7. The method of claim 6, wherein the steps of separating whole blood into first and second constituents and separating the mononuclear cells from the red blood cells of the first mixture take place substantially at the same time.

8. The method of claim 7, further comprising the step of directing remaining whole blood into the second compartment when an optical sensor disposed upstream of the second compartment detects that fluid leaving the first compartment has adequate clarity.

9. The method of claim 1, wherein the step of separating whole blood into first and second constituents is performed by a spinning membrane separator.

10. The method of claim 1, wherein the plasma replacement fluid comprises at least one of fresh frozen plasma and albumin.

11. The method of claim 1, wherein the steps of separating whole blood into first and second constituents and separating the mononuclear cells from the red blood cells of the first mixture take place substantially at the same time.

12. The method of claim 1, wherein the plasma replacement fluid comprises purified plasma.

13. The method of claim 12, further comprising the step of performing extracorporeal photopheresis on the mononuclear cells, and wherein the plasma replacement fluid contains fewer proteins, lipids, and/or bilirubin than does the plasma.

14. The method of claim 12, wherein the step of separating whole blood into first and second constituents is performed by a centrifugal separator.

15. The method of claim 12, wherein the step of separating whole blood into first and second constituents is performed by a spinning membrane separator.

16. The method of claim 12, wherein the mononuclear cells comprise at least one of lymphocytes, monocytes, and stem cells.

17. The method of claim 12, wherein the purified plasma is formed by flowing the first constituent separated from the second constituent through a plasma adsorption column.

18. The method of claim 1, wherein said separating the mononuclear cells from the red blood cells of the first mixture includes optically monitoring an interface between separated components of the first mixture.

19. The method of claim 1, wherein said separating the mononuclear cells from the red blood cells of the first mixture includes optically monitoring a separated component of the first mixture flowing through a tubing line.

20. A method of collecting mononuclear cells, comprising:
- separating plasma from cellular components of whole blood using a separator, the cellular components including mononuclear cells and red blood cells;
- combining the cellular components with plasma replacement fluid to form a first mixture including the mononuclear cells and the red blood cells; and
- separating the mononuclear cells from the red blood cells of the first mixture, wherein
  - said separating plasma from cellular components of whole blood using the separator includes not separating the mononuclear cells from the plasma and the other cellular components as part of a separate constituent, and
  - said separating the mononuclear cells from the red blood cells of the first mixture includes optically monitoring the first mixture and/or a separated component of the first mixture.

21. The method of claim 20, wherein said separating the mononuclear cells from the red blood cells of the first mixture includes optically monitoring an interface between separated components of the first mixture.

22. The method of claim 20, wherein said separating the mononuclear cells from the red blood cells of the first mixture includes optically monitoring a separated component of the first mixture flowing through a tubing line.

23. A method of collecting mononuclear cells, comprising:
- separating whole blood into only first and second constituents using a separator, the first constituent comprising plasma and the second constituent including mononuclear cells and red blood cells;
- combining the second constituent with plasma replacement fluid to form a first mixture including the mononuclear cells and the red blood cells; and
- separating the mononuclear cells from the red blood cells of the first mixture, wherein
  - said separating whole blood into only first and second constituents using the separator includes not separating the mononuclear cells as part of a third constituent, and
  - said separating the mononuclear cells from the red blood cells of the first mixture includes optically monitoring the first mixture and/or a separated component of the first mixture.

24. The method of claim 23, wherein said separating the mononuclear cells from the red blood cells of the first mixture includes optically monitoring an interface between separated components of the first mixture.

25. The method of claim 23, wherein said separating the mononuclear cells from the red blood cells of the first mixture includes optically monitoring a separated component of the first mixture flowing through a tubing line.

* * * * *